US012800563B2

(12) United States Patent
Dörksen et al.

(10) Patent No.: US 12,800,563 B2
(45) Date of Patent: Nov. 17, 2026

(54) APPARATUS FOR DETERMINING THE PRESENCE OF A CHARACTERISTIC OF A SAMPLE, AND IN PARTICULAR FOR SEX DETERMINATION OF A FERTILISED BIRD EGG, USE, AND METHOD

(71) Applicant: TECHNISCHE HOCHSCHULE OSTWESTFALEN-LIPPE, Lemgo (DE)

(72) Inventors: Helene Dörksen, Kaltenkirchen (DE); Harald Klausing, Horn-Bad Meinberg (DE); Jürgen Krahl, Lemgo (DE)

(73) Assignee: TECHNISCHE HOCHSCHULE OSTWESTFALEN-LIPPE, Lemgo (DE)

( * ) Notice: Subject to any disclaimer, the term of this patent is extended or adjusted under 35 U.S.C. 154(b) by 0 days.

(21) Appl. No.: 18/851,946

(22) PCT Filed: Mar. 24, 2023

(86) PCT No.: PCT/EP2023/057650
§ 371 (c)(1),
(2) Date: Sep. 27, 2024

(87) PCT Pub. No.: WO2023/186734
PCT Pub. Date: Oct. 5, 2023

(65) Prior Publication Data
US 2025/0216371 A1 Jul. 3, 2025

(30) Foreign Application Priority Data
Mar. 29, 2022 (DE) ..................... 10 2022 107 397.1

(51) Int. Cl.
*G01N 33/08* (2006.01)
*G01N 21/64* (2006.01)
*G16C 60/00* (2019.01)

(52) U.S. Cl.
CPC ....... *G01N 33/085* (2013.01); *G01N 21/6408* (2013.01); *G01N 21/6486* (2013.01); *G16C 60/00* (2019.02); *G01N 2021/6421* (2013.01)

(58) Field of Classification Search
CPC ............. G01N 33/085; G01N 21/6408; G01N 21/6486; G01N 2021/6421; G16C 60/00; A01K 45/007; A01K 45/00
See application file for complete search history.

(56) References Cited

U.S. PATENT DOCUMENTS 6,272,376 B1 * 8/2001 Marcu .................. A61B 5/0084 600/477
7,041,439 B2 * 5/2006 Phelps ..................... G01N 1/34 435/235.1
(Continued)

FOREIGN PATENT DOCUMENTS

CN 109444106 A 3/2019
CN 108983051 B 2/2021
(Continued)

OTHER PUBLICATIONS

Nikolay A. Denisov: “titleComparison of competing fiber optic probes for tissue fluorescence analysis /title”, Proceedings of SPIE, Visual Communications and Image Processing 2005, vol. 4161, Nov. 16, 2000 (Nov. 16, 2000), pp. 234-243, XP055051756, Visual Communications and Image Processing 2005.
(Continued)

*Primary Examiner* — Tarifur R Chowdhury
*Assistant Examiner* — Carlos Perez-Guzman
(74) *Attorney, Agent, or Firm* — REISING ETHINGTON, P.C.

(57) ABSTRACT

A device for determining the presence of a characteristic of a sample includes a light source for emitting pulsed excitation radiation, a detection device for detecting an autofluorescence radiation emitted by the sample, and a computer-
(Continued)

based evaluation device. The detection device is configured to detect the autofluorescence radiation of the sample in a time-resolved manner at different wavelengths by means of time-correlated single photon counting and to provide the evaluation device with two-dimensional data with a wavelength dimension and a time dimension. The evaluation device is configured to classify the provided data into classes by means of a classifier. The evaluation device is configured to identify specific wavelengths to be prioritized during the classification on the basis of features formed in the time dimension of the data.

10 Claims, 3 Drawing Sheets

(56) References Cited

U.S. PATENT DOCUMENTS

| | | | | |
|---|---|---|---|---|
| 7,950,349 | B1 | 5/2011 | Rollins | |
| 8,364,247 | B2 | 1/2013 | Opitz et al. | |
| 8,624,190 | B2 | 1/2014 | Steiner et al. | |
| 9,804,092 | B2 | 10/2017 | Zeng et al. | |
| 9,937,357 | B2 | 4/2018 | Szasz et al. | |
| 10,852,284 | B2 | 12/2020 | Steiner et al. | |
| 10,914,684 | B2 | 2/2021 | Zhou et al. | |
| 11,378,565 | B2 | 7/2022 | Preusse et al. | |
| 12,198,333 | B2 | 1/2025 | Kwon | |
| 2004/0162489 | A1 | 8/2004 | Richards-Kortum et al. | |
| 2012/0058052 | A1 | 3/2012 | Decuypere et al. | |
| 2012/0318981 | A1 | 12/2012 | Steiner et al. | |
| 2014/0293277 | A1 | 10/2014 | Subbiah et al. | |
| 2015/0082465 | A1* | 3/2015 | Kato | G01N 21/6486 506/10 |
| 2016/0290924 | A1* | 10/2016 | Nuutinen | G01N 21/6408 |
| 2017/0205353 | A1* | 7/2017 | Galli | G01N 33/4833 |
| 2019/0376012 | A1* | 12/2019 | Pedersen | G01N 21/6408 |
| 2019/0383782 | A1 | 12/2019 | Steiner et al. | |
| 2020/0110068 | A1* | 4/2020 | Green | G01N 21/84 |
| 2020/0408693 | A1 | 12/2020 | Zhou et al. | |
| 2021/0248429 | A1 | 8/2021 | Steiner | |
| 2021/0382290 | A1 | 12/2021 | Rigneault et al. | |
| 2022/0328188 | A1* | 10/2022 | Sanchez | G16H 10/40 |
| 2023/0081662 | A1 | 3/2023 | Dörksen et al. | |
| 2024/0069000 | A1* | 2/2024 | Hurlin | G01N 33/085 |
| 2024/0407341 | A1 | 12/2024 | Steiner et al. | |

FOREIGN PATENT DOCUMENTS

| | | | |
|---|---|---|---|
| CN | 113850174 | A | 12/2021 |
| DE | 60208823 | T2 | 8/2006 |
| DE | 102010006161 | B3 | 1/2011 |
| DE | 102016004051 | B3 | 7/2017 |
| DE | 102020000214 | A1 | 7/2021 |
| DE | 102021127696 | B3 | 3/2023 |
| EP | 2336751 | A1 | 6/2011 |
| JP | H02193027 | A | 7/1990 |
| JP | 6127142 | B2 | 5/2017 |
| KR | 20230023872 | A | 2/2023 |
| WO | WO2017174337 | A1 | 10/2017 |
| WO | WO2018001437 | A1 | 1/2018 |
| WO | WO2019170887 | A1 | 9/2019 |
| WO | WO2020098243 | A1 | 5/2020 |
| WO | WO2021144420 | A1 | 7/2021 |
| WO | WO2023161532 | A1 | 8/2023 |
| WO | WO2023240122 | A1 | 12/2023 |

OTHER PUBLICATIONS

European Office Action for European Application No. 21 700 896.0-1001 dated Dec. 12, 2025 (86 pages).

German Office Action for German Patent Application No. 10 2024 114 348.7 dated Apr. 1, 2025 (12 pages).

Helene Dörksen et al.; Combinatorial Refinement of Feature Weighting for Linear Classification; 2014 IEEE Emerging Technology and Factory Automation (ETFA) 978-1-4799-4845-1/14 (7 pages).

Helene Dörksen et al.; Linear Classification of Badly Conditioned Data; 978-1-5386-7108-5/18; pp. 654-660 (7 pages).

Christopher James Langmead et al.; A Maximum Entropy Algorithm for Rhythmic Analysis of Genome-Wide Expression Patterns; Proceedings of the IEEE Computer Society Bioinformatics Conference (CBS '02); 0-7695-1653-X/02; (9 pages).

Galli, Roberta [et al.]: In ovo sexing of chicken eggs by fluorescence spectroscopy. In: Analytical and bioanalytical chemistry, vol. 409, 2017, No. 5, S. 1185-1194.

Perri, A. {et al.): Time- and frequency-resolved fluorescence with a single TCSPC detector via a Fourier-transform approach. In: Optics express, vol. 26, 2018, No. 3, S. 2270-2279.

Shcheslavskiy V I et at: "Multiparametric Time-Correlated Single Photon Counting Luminescence Microscopy", Biochemistry (Moskow), Pleiades Publishing, Moscow, Bd. 84, Nr. 1, Apr. 19, 2019 (Apr. 19, 2019), pp. 51-68.

Rajapaksha, Nipuna [et al.]: Supervised machine learning algorithm selection for condition monitoring of induction motors. Proceedings : 2021 IEEE southern power electronics conference (SPEC), Dec. 6-9, 2021. 10 S.—ISBN 978-1-6654-3623-6.

International Search Report for International Application No. PCT/EP2023/057650 dated Jun. 7, 2023 (4 pages).

English Translation of International Search Report for International Application No. PCT/EP2023/057650 dated Jun. 7, 2023 (3 pages).

International Search Report for International Application No. PCT/EP2025/064140 dated Jul. 14, 2025 (36 pages).

Mcgown L B et al: "Total Lifetime Distribution Analysis for Fluorescence Fingerprintingand Characterization", Applied Spectroscopy, The Society for Applied Spectroscopy. Baltimore, US, vol. 49, No. 1, Jan. 1, 1995 (Jan. 1, 1995), pp. 60-66, XP000486663, ISSN: 0003-7028, DOI: 10.1366/0003702953963427.

Shen C-H: "Feature Extraction and 1.11 Classification of Heart Murmurs Based on 13-15 Acoustic Qualities," IRBM, Elsevier, Amsterdam, NL, vol. 43, No. 5, Feb. 18, 2021 (Feb. 18, 2021), pp. 470-478, XP087182741, ISSN: 1959-0318, DOI: 10.1016/J.IRBM.2021.02.002 [found on Feb. 18, 2021].

Indian Office Action regarding Application No. 202417073205, mailed Jul. 20, 2026.

* cited by examiner

APPARATUS FOR DETERMINING THE PRESENCE OF A CHARACTERISTIC OF A SAMPLE, AND IN PARTICULAR FOR SEX DETERMINATION OF A FERTILISED BIRD EGG, USE, AND METHOD

INTRODUCTION

The disclosure relates to a device for determining the presence of a characteristic in a sample, and preferably for determining the sex of a fertilized bird's egg.

The disclosure further relates to a method for in-ovo sex determination of a fertilized bird's egg.

The disclosure also relates to the use of the above device.

There is currently an effort to be able to determine the sex of a future chick already in the fertilized chicken egg.

In the course of development, different fluorophores are produced in the bird's egg in male and female chicks. Due to their complex structure, the corresponding molecules have an unpredictable fluorescence characteristic. During fluorescence, energetic transitions from the excited state to the ground state of the molecule are observed. This process is time-dependent.

Document WO 2021/144420 A1 describes a device and a method for optical in-ovo sex determination of a fertilized bird's egg. The device comprises a light source for emitting excitation radiation to excite fluorescence in an area inside the bird's egg, a spectroscopic device for time-resolved and/or spectrally resolved analysis of fluorescence radiation emitted from the area inside the bird's egg, and an evaluation unit for sex determination from the data determined by means of the spectroscopic device.

SUMMARY

On this basis, it is an object per an embodiment of the disclosure to provide means with which the accuracy of in-ovo sex determination is increased in a simplified design of the device.

According to an embodiment, a device for determining the presence of a characteristic of a sample, and preferably for determining the sex of a fertilized bird's egg, is provided, comprising

- a light source for emitting pulsed excitation radiation,
- a detection device for detecting autofluorescence radiation emitted by the sample, and
- a computer-based evaluation unit,
- wherein the detection device is configured to detect the autofluorescence radiation of the sample in a time-resolved manner at different wavelengths by means of time-correlated single photon counting and to provide the evaluation device with two-dimensional data having a wavelength dimension and a time dimension,
- wherein the evaluation device is configured to classify the provided data into classes by means of a classifier, wherein at least one class represents the characteristic of the sample, wherein the evaluation device is configured to identify specific wavelengths to be prioritized in the classification based on features formed in the time dimension of the data, and wherein the evaluation device is configured to consider the data at the specific wavelengths in a prioritized manner in order to determine the presence of the characteristic of the sample.

Furthermore, the disclosure relates to a method for in-ovo sex determination of a fertilized bird's egg, comprising the steps of

- emitting pulsed excitation radiation for excitation of autofluorescence in an area inside the bird's egg, on an egg membrane of the bird's egg and/or on the egg shell of the bird's egg by means of a light source,
- time-resolved detection of the autofluorescence radiation emitted from the area inside, from the egg membrane and/or from the egg shell of the bird's egg by means of a detection device at different wavelengths by time-correlated single photon counting,
- providing an evaluation device with two-dimensional data with a wavelength dimension and a time dimension by the detection device,
- sex determination of the fertilized bird's egg from the provided two-dimensional data by means of the evaluation device by classifying the provided data by means of a classifier into two classes, wherein a first class represents a male sex of the fertilized bird's egg and a second class represents a female sex of the fertilized bird's egg, wherein during the classification, specific wavelengths to be prioritized are identified on the basis of features formed in the time dimension of the data, and sex determination of the bird's egg by considering the data at the specific wavelengths in a prioritized manner.

The method can be carried out by use of the above device.

It was found that when classifying two-dimensional data into classes to determine the presence of a characteristic of the sample, improved accuracy is achieved for data with a higher time resolution. Furthermore, it was found that the information included in the decay behavior of the autofluorescence radiation is not equally relevant at all wavelengths, but that specific wavelengths can be identified whose prioritized consideration in the classification allows for improved accuracy. Accordingly, the device and the method have improved accuracy by detecting the autofluorescence radiation by means of single photon counting and by identifying the specific wavelengths.

In other words, in relation to in-ovo sex determination of a fertilized bird's egg, knowledge of the lifetime and decay profile of excited molecular states (time dimension of the two-dimensional data) is relevant for the identification of the sex of the fertilized bird's egg, in addition to the energy of the emitted photons (wavelength dimension of the two-dimensional data), wherein the time dimension at the specific wavelengths with respect to other wavelengths includes more meaningful information and is accordingly prioritized in the evaluation.

With respect to the device, it is envisaged that the device comprises the light source for emitting the pulsed excitation radiation, the detection device for detecting the autofluorescence radiation at several different wavelengths by means of time-correlated single photon counting, and the computer-based evaluation unit.

In order to detect the autofluorescence radiation with high time resolution, in the present case, the autofluorescence radiation is detected by means of time-correlated single photon counting, TCSPC. Instead of using a method in which the complete spectrum is recorded by means of an ICCD camera at different times after an excitation pulse of the light source, as in the prior art (WO 2021/144420 A1), the complete spectrum is not recorded after each excitation pulse in TCSPC.

In TCSPC, individual photons of a periodic light signal—in this case the autofluorescence radiation—are detected and the respective times between the excitation pulse of the pulsed excitation radiation and the arrival of the photon in the detection device are determined. In other words, the fluorophores in the sample to be examined—preferably the bird's egg—are excited by means of the pulsed excitation radia-tion of the light source. The time measurement is started by the excitation pulse and the photon emitted during the transition from the excited state to the ground state stops the measurement. The measurement is repeated many times and the individual temporally correlated photons (in relation to the excitation pulse) are sorted into a so-called TCSPC histogram according to their measured time. The TCSPC histogram represents the temporal course of the autofluorescence radiation after excitation. Preferably, the TCSPC histogram generated by means of the detection device has a class width, also referred to as bin width, for the histogram classes of 1 ps to 50 ps, preferably of 10 ps to 20 ps. Preferably, the class width of the TCSPC histogram can be adapted to the device and/or the sample to be examined. Further preferably, a temporal resolution of the entire device—and particularly preferably a full width at half maximum (FWHM) of the instrument response function (IRF)—is taken into account when adapting the class width of the TCSPC histogram. The FWHM of the IRF is essentially dependent on the light source and a pulse length generated by the light source and/or on a detector element of the detection device.

In other words, the complete spectrum (wavelength dimension of the two-dimensional data) is not measured at different points in time, but rather the TCSPC histogram representing the temporal course of the autofluorescence radiation—i.e. the time dimension of the two-dimensional data—is determined by means of a large number of measurement cycles—typically in the range of 106, wherein each measurement cycle is started by an excitation pulse of the light source.

The detection device is configured to provide the evaluation device with two-dimensional data with a wavelength dimension and a time dimension. The two-dimensional data preferably represent the decay behavior of the autofluorescence (time dimension) at the different wavelengths (wavelength dimension). The two-dimensional data can be forwarded to the evaluation device, for example, in the form of an m×n matrix. Preferably, the two-dimensional data in the time dimension have more data points than in the wavelength dimension. This has proven to be particularly advantageous, per certain embodiments, for determining the presence of a characteristic of the sample and especially for determining the sex of the bird's egg.

On the basis of the two-dimensional data, the evaluation unit can identify the specific wavelengths to be prioritized. This is achieved by the classifier classifying the provided data into classes. Depending on the sample and possible characteristics of the sample, there may be a different number of classes, wherein the classes represent possible characteristics of the sample.

Preferably, the identification of the specific wavelengths is based on the principle of supervised machine learning, wherein the specific wavelengths are calculated from the two-dimensional data representing the samples of corresponding classes by means of the evaluation device. According to an embodiment, the evaluation device is configured in such a way that one or more characteristic features and associated class-specific separating properties can be and/or are calculated from the decay behavior of the autofluorescence of the wavelengths—that is, from the time dimension of the two-dimensional data. The characteristic features can be calculated from time series representing individual wavelengths. Alternatively, the characteristic features can be calculated from linear combinations of time series representing individual wavelengths.

The evaluation device is preferably configured in such a way that those wave-lengths with relatively higher separation properties are identified as specific wave-lengths. Only as many specific wavelengths are identified as are needed to achieve the desired and/or sufficient classification rate for the sample under consideration. The non-prioritized wavelengths preferably do not contribute to the separation of the classes and are therefore neglected and not considered further for the classification.

It has been shown that a classification without prioritization of the wavelength, which is equivalent to a classification in which all wavelengths are given equal priority, has a lower accuracy than a classification with prioritization of the wavelength. Further preferably, a metric of the separation property analysis is considered in the identification of the specific wavelengths. In the context of the method for in-ovo sex determination, it is preferably provided that a linear discriminant analysis (LDA) is used as the metric. LDA is particularly suitable for data that exhibit a Gaussian distribution.

Preferably, it is provided that the evaluation device is configured to take into account the data at the specific wavelengths in a prioritized manner in determining the presence of the characteristic of the sample, and in particular to take into account features formed in the time dimension of the data at the specific wavelengths in a prioritized manner. In terms of the method, the sex of the bird's egg is thus determined by taking into account the data at the specific wavelengths in a prioritized manner and in particular by taking into account the features formed in the time dimension of the data at the specific wavelengths in a prioritized manner.

The device for determining the presence of a characteristic of a sample can not only be used to determine the sex of the fertilized bird's egg. The device is also suitable for classifying samples with regard to other characteristics. In this case, it is not necessary to prepare the samples in any special way. In particular, the described device can be used when samples and/or objects are authenticated with regard to a characteristic, i.e. when it is determined whether an asserted characteristic of the sample is true, as for example in the case of authentication of counterfeit banknotes, or in the case of authentication of an asserted characteristic of origin of a foodstuff. The device is particularly suitable, per an embodiment, for authentications in which the sample that has the asserted characteristic—for example, the original banknote—is very similar to the sample that does not have the asserted characteristic—in this example, the counterfeit banknote.

According to another embodiment, the detection device is configured to detect the autofluorescence radiation of the sample at the specific wave-lengths identified as prioritized by use of time-correlated single photon counting in a time-resolved manner and to provide the evaluation device with two-dimensional data with the wavelength dimension and the time dimension, wherein the wave-length dimension corresponds to the number of specific wavelengths and wherein the evaluation device is configured to classify the provided data into the classes by means of the classifier. In other words, the evaluation device determines on the basis of the two-dimensional data whether the characteristic is present in a sample or not. This is achieved by the detection device determining the TCSP histo-gram targetedly at the specific wavelengths and thus only provides the evaluation device with time series at the specific wavelengths. This enables to achieve a high accuracy in determining the characteristic of the sample without having to detect the autofluorescence at all possible wavelengths.

According to an embodiment, it is envisaged with respect to the device that the light source is configured as a pulsed excitation laser system or as a pulsed LED. The light source is configured in such a way that the sample is excited with a wavelength in the UV range, particularly in a range around 266 nm and/or at 266 nm. It is further preferred, per an embodiment, that the light source is configured to emit as excitation radiation a radiation with a wave-length in a range from greater than or equal to 250 nm to less than or equal to 520 nm, greater than or equal to 280 nm to less than or equal to 400 nm.

With regard to the excitation laser system, it is further provided, per an embodiment, that the excitation laser system is configured as a solid-state laser with a frequency conversion stage and/or optical parametric oscillator (OPO). Preferably, per an embodiment, a titanium-sapphire laser with a frequency conversion stage and/or optical parametric oscillator (OPO) is used. Alternatively, the excitation laser system is configured as a frequency-quadrupled Nd:YAG laser with an optional optical parametric oscillator. Further, the excitation laser system is a diode laser system, preferably in a MOFA configuration. Further, the excitation laser system is configured as a master oscillator power amplifier (MOPA) and/or as a master oscillator fiber amplifier (MOFA). MOPA and/or MOFA are laser systems that use a seed laser as a master oscillator to provide an amplifier unit with the characteristics of the emission radiation at high coherence. Particular preferably, per an embodiment, an infrared laser diode and/or a near-infrared laser diode is used as the master oscillator or seed laser to provide a multi-stage fiber amplifier with the characteristics of the laser emission in the MOFA arrangement. In addition, the wavelengths of the second, third and/or fourth harmonics can be generated by nonlinear frequency conversion using birefringent crystals. This allows for a particularly compact and portable measurement setup.

Alternatively it may be provided that the light source is configured as a pulsed LED. LEDs have the advantage of being cost-effective. In addition, the increased spectral bandwidth of the LED emission compared to the excitation laser system can have the advantage that a larger number of absorption processes in different fluorophores in the sample are induced by the LED as a light source. Preferred LEDs for use as a light source emit at wavelengths in the UV range, particularly at 265 nm, 285 nm, 310 nm and/or >310 nm, with a spectral bandwidth of ±10 nm each. In addition, the spectral bandwidth can be reduced by appropriate interference filters.

In order to achieve the highest possible time resolution in the detection of the auto-fluorescence radiation, it is advantageous per an embodiment if the length of the excitation pulse of the pulsed excitation radiation is as short as possible. In this context, it is provided that the light source is configured to emit pulsed excitation radiation with a pulse length of ≤500 ps, preferably ≤200 ps, particularly preferably ≤100 ps, per embodiments. This is possible in particular by designing the light source as a pulsed excitation laser system. Alternatively, it is envisaged that the light source is configured to emit pulsed excitation radiation with a pulse length of ≤5 ns, preferably ≤2 ns, particular preferably ≤1 ns, per embodiments. This is particularly possible in connection with the design of the light source as an LED. The short pulse length increases the time resolution and thus the accuracy when determining the presence of a characteristic of the sample.

Since a large number of measurement cycles are carried out to generate the TCSPC histogram for the autofluorescence radiation detected by TCSPC, it is also provided per an embodiment that the light source is configured to emit pulsed excitation radiation at a pulse repetition rate of ≥10 MHz. This considerably reduces the time required to detect the two-dimensional data.

In addition, when using TCSPC to detect the autofluorescence radiation, the excitation intensity is preferably kept, per an embodiment, so low that the detection probability for a fluorescence photon per excitation cycle is less than or equal to 1, i.e. at most one photon is detected during each excitation cycle. In this context, according to an embodiment it is provided that the device comprises an optical attenuator in the beam path between the light source and the sample for adjusting an energy of the excitation radiation. Preferably, this is a variable attenuator, in particular a variable laser beam attenuator. The attenuator is further configured such that the energy per pulse for excitation of the sample is so small that the detection probability for a fluorescence photon per excitation cycle is less than or equal to 1. Typically, single-photon statistics can be achieved if a counting pulse at the detector element is triggered on average by only one of 20 to 100 excitation pulses. In other words, this means that a count rate at the detector element lies in the range of 1-5% of the excitation rate. This means, for example, that at a pulse repetition rate of 80 MHz, the attenuator is set so that the average count rate of the detector element does not exceed 4 MHZ. This is an easy way to ensure that the TCSPC histogram is not affected by systematic measurement errors caused by the so-called pile-up effect.

As already mentioned, the detection device is configured to detect the autofluorescence radiation of the sample at different wavelengths by use of time-correlated single photon counting in a time-resolved manner. According to an embodiment, it is envisaged in this context that the detection device for detecting the autofluorescence radiation at different wavelengths comprises a monochromator, a spectrograph and/or a spectrometer. This greatly simplifies the detection of the autofluorescence radiation at different wavelengths. The detection device can, for example, comprise a stepwise rotatable diffraction grating and a monochromator. This has the advantage, per an embodiment, that a broad spectral range, for example from 370 nm to 700 nm, can be scanned stepwise and a TCSPC histogram can be recorded for each of the wavelengths scanned.

In an alternative embodiment, the device for spectral separation comprises a replaceable interference filter between the sample and a detector element of the detection device. The interference filter can be replaced by another interference filter depending on the wavelength to be detected. This is advantageous, per an embodiment, when the autofluorescence radiation of the sample is detected in a time-resolved manner by use of time-correlated single photon counting at the specific wavelengths identified as prioritized. In a further alternative, the detection device comprises several detector elements and one or more beam splitters that split the autofluorescence radiation into several partial beams. In this way, a TCSPC histogram can be recorded for each partial beam by means of a exchangeable interference filter and by means of the detector element.

Furthermore, it is envisaged in connection with the detection device that the detection device comprises a hybrid photomultiplier (hybrid PMT)—also called a hybrid photodetector—as the detector element. Preferably, per an embodiment, the detector element is a combination of a front-end PMT with an avalanche photodiode (APD) as an additional amplification stage. More preferably, the detector element is configured to multiply a photoelectron released in the latter amplification stage by a factor of 50,000 to 150,000. More preferably, the detector element is configured to achieve a time resolution of about 120 ps (FWHM of the instrument response function (IRF)).

The detector element is further configured, per an embodiment, as a multi-channel detector, preferably as a multi-channel plate PMT (MC-PMT), so that several different wave-lengths can be detected simultaneously. For example, the multi-channel detector has 16 channels for detection. The configuration of the detection device as a combination of a spectrograph with a fixedly positioned diffraction grating and an MCP-PMT allows simultaneous multispectral detection with an equidistant subdivision of the total wave-length range detected. The subdivision and the width of the wave-length intervals depend on the number of channels of the MCP-PMT.

The detection device is configured, per an embodiment, to receive the autofluorescence radiation with a wavelength in a range from greater than or equal to 200 nm to less than or equal to 700 nm.

In connection with the TCSPC histogram, it is envisaged, according to an embodiment, that the device for generating an electrical trigger signal, which can be generated synchronously with the excitation pulse, comprises a pulse signal generator. In this way, a fast voltage ramp can be started by means of a time-amplitude converter with the aid of the electrical trigger signal generated synchronously with the excitation pulse, which ramp is stopped by the measurement of a photon of the autofluorescence radiation. For example, the excitation laser system can be used directly as the pulse signal generator, which provides the electrical trigger signal. Alternatively, the electrical trigger signal can be generated by use of a trigger photodiode, for which a fraction of the excitation radiation is decoupled via a beam splitter.

In addition, in this context, it is further provided that the detector element generates an electrical output pulse for each detected photon, which pulse is formed into a standard pulse in a fast discriminator. In this way, the detector standard pulse can stop the voltage ramp started by the electrical trigger signal of the excitation laser system. A voltage is thus associated with each stop instant, so that the TCSPC histogram can be generated in this way.

According to another embodiment, it is provided that the device comprises a long-pass edge filter arranged in the beam path between the sample and the detection device and adapted to filter a wave-length of the excitation radiation. In this way, the excitation radiation scattered at the sample can be easily filtered out.

According to another embodiment, it is also provided that the device comprises an optical component arranged in the beam path between the sample and the detection device and adapted to focus the fluorescence emitted by the sample onto the detection device. The optical component can, for example, be configured as a lens and in particular as a converging lens. In particular when using LEDs as the light source, it can moreover be provided that the device comprises optical components for focusing the excitation radiation between the light source and the sample.

With regard to the irradiation of the sample, according to an embodiment it is provided that the device is configured to irradiate the sample in free space with the excitation radiation and is configured in such a way that the autofluorescence radiation emitted at an angle not equal to zero to the excitation radiation is directed in the free space onto the detection device. In this context, free space means that the light is not transported via a fiber-based light guide system, but propagates freely in space. In this embodiment, thus, the device does not have a fiber-based light guide system, such as an optical fiber, for guiding the light. By dispensing with a fiber-based light guide system, it can be prevented that losses of the pulse energy in the light guide system and/or a broadening of the excitation pulse occur, which can be particularly problematic at excitation wavelengths in the UV range. In addition, the device without a fiber-based light guide system has the advantage, per an embodiment, that a measuring head for irradiating the sample and/or for receiving the fluorescence radiation from the sample can be dis-pensed with, so that the device has a very simple structure.

In connection with the propagation in free space, according to an embodiment it is provided that the device comprises a shielding device for shielding ambient light. Particularly, the shielding device is a sample chamber designed in such a way that the excitation radiation emitted by the light source can propagate to the sample present in the sample chamber shielded from ambient light, and that the autofluorescence radiation emitted by the sample can propagate to the detection device, shielded from ambient light.

According to an alternative embodiment it is provided that the device comprises a measuring head, a) wherein the measuring head is configured to emit the excitation radiation into and/or onto the sample, or
b) the measuring head is configured to receive the autofluorescence radiation out of and/or from the sample, or
c) the measuring head is configured to emit the excitation radiation into and/or onto the sample and to receive the autofluorescence radiation out of and/or from the sample.

It may be provided that the measuring head is connected to a light guide system. More preferably, per an embodiment, it may in particular in the case of c) be a Y-shaped light guide system with two light guide strands which are merged on the side of the measuring head.

In an embodiment, it is provided that the light guide strands are formed as a light guide bundle whose individual light guides are intertwined, for example twisted, on the side of one end of the measuring head. Alternatively, the individual light guides can be uniformly distributed over the generally circular cross-section. Alternatively, the light guides guiding the excitation radiation can, for example, be arranged in a circular pattern in the inner area of the cross-section, and the light guides guiding the autofluorescence radiation can, for example, be arranged in a concentric ring around the outside. In this way, the emission of the excitation radiation into and/or onto the sample and the reception of the autofluorescence radiation out of and/or from the sample can be realized in a simple manner with the same measuring head.

With regard to the computer-based evaluation device, as already mentioned, it is envisaged that the evaluation device is configured to classify the provided data into classes by means of the classifier, wherein at least one class represents the characteristic of the sample. In this context, it is provided that the classifier is a linear classifier. A linear classifier separates the classes along a linear hyperplane. It is further provided that the classifier is constructed by means of feature selection with the aid of linear discriminant analysis based on training data. In other words, it is an evaluation device based on machine learning. Preferably, the evaluation device learns from examples—the training data—and can generalize them after the learning phase is completed. To this end, algorithms in machine learning build a statistical model based on the training data.

According to a further embodiment it is provided that the evaluation device is an evaluation device based on so-called feature engineering. Feature engineering is a form of data preparation and describes the selection and preparation of features that are used to create a machine learning model. In this context, it is also provided that the features formed in the time dimension of the data include the central moments of the first order (mean value), second order (standard deviation) and third order (skewness), and/or that the features formed in the time dimension of the data are histogram-based features, signal-series-based features and/or transformation-based features. Preferably, per an embodiment, it can also be provided that the evaluation device is arranged to eliminate features with weak separating properties, preferably with the aid of Fischer's linear discriminant analysis (LDA).

Furthermore, according to an embodiment it is provided that the evaluation device is configured to identify the specific wavelengths by means of machine learning. In this way, good accuracy can be achieved in determining the presence of a characteristic of the sample by use of two-dimensional data that have a low resolution in the wavelength dimension despite the low spectral resolution.

According to an embodiment it is provided that the evaluation device is configured to determine the sex of the fertilized bird's egg taking into consideration the two-dimensional data. In other words, the device is preferably used to determine the sex of the fertilized bird's egg. In this context, it is further provided that the evaluation device is configured to classify the provided data into two classes by means of the classifier, wherein a first class represents the characteristic "male sex" and a second class represents the characteristic "female sex" of the bird's egg as a sample.

As already mentioned, the disclosure also relates to the method for in-ovo sex determination in the fertilized bird's egg, comprising the steps of

- emitting pulsed excitation radiation for excitation of autofluorescence in an area inside the bird's egg, on an egg membrane of the bird's egg and/or on the egg shell of the bird's egg by means of a light source,
- time-resolved detecting the autofluorescence radiation emitted from the area inside, from the egg membrane and/or from the egg shell of the bird's egg by means of a detection device at different wavelengths by time-correlated single photon counting,
- providing an evaluation device with two-dimensional data with a wavelength dimension and a time dimension by the detection device,
- sex determination of the fertilized bird's egg from the provided two-dimensional data by means of the evaluation device by classifying the provided data by means of a classifier into two classes, wherein a first class represents a male sex of the fertilized bird's egg and a second class represents a female sex of the fertilized bird's egg, wherein during the classification, specific wavelengths to be prioritized are identified on the basis of features formed in the time dimension of the data, and sex determination of the bird's egg by prioritized consideration of the data at the specific wavelengths.

In the embodiment of the method for in-ovo sex determination of the fertilized bird's egg, it is also envisaged that the autofluorescence in an area inside the bird's egg, of the egg membrane of the bird's egg and/or of the egg shell of the bird's egg is excited by means of a light source. Preferably, per an embodiment, the autofluorescence is excited on the egg membrane of the bird's egg and/or on the egg shell of the bird's egg. Furthermore, per an embodiment, it is provided that the area inside the bird's egg is preferably a bloodstream area and/or an area of embryonic structures. It is further provided that the bird's egg does not have to be opened to determine the sex. Instead, it is possible to determine the sex directly on, at and/or through the eggshell of the bird's egg by use of the device and/or method described. In other words, it is provided per an embodiment that the emission of pulsed excitation radiation is directed onto the eggshell of the bird's egg. This has the advantage that the process is very easy and quick to perform and the risk of infection of the bird's egg is greatly reduced. Which of the areas is selected may depend in particular on the developmental stage in the fertilized bird's egg. Furthermore, it is not necessary for the bird's egg to be incubated. The sex can also be determined in an unincubated bird's egg.

Alternatively, the bird's egg can be opened to determine the sex. In this embodiment, it is preferable to create a hole in the egg shell of the bird's egg. The hole should preferably have a hole size with a dimension or a diameter D in the range 0.5 mm≤D≤3 mm. In particular it is provided per an embodiment that the hole is created without perforating any egg membrane lying under the egg shell and/or without perforating any shell membrane and/or egg membrane lying under the egg shell. The measurement of the autofluorescence can be carried out at the amniotic membrane, the shell membrane and/or the egg membrane.

According to a further alternative embodiment of the method, it may be provided that an interior of the bird's egg and/or the area inside the bird's egg is removed from the egg shell and the method steps are carried out accordingly outside the egg shell.

According to a another embodiment, it is also provided that the method comprises the steps of

- time-resolved detection of the autofluorescence radiation emitted from the area inside, from the egg membrane and/or from the egg shell of the bird's egg by means of the detection device at the specific wavelengths by time-correlated single photon counting, and
- providing the evaluation device with two-dimensional data with a wavelength dimension and a time dimension by the detection device, wherein the wave-length dimension corresponds to the number of specific wavelengths.

Thus, as soon as the evaluation device has identified the specific wavelengths to be prioritized, the autofluorescence can be detected targetedly at the specific wave-lengths for sex recognition for further samples. The other wavelengths do not need to be considered further.

As already mentioned, the device can be used not only to determine the sex of fertilized bird's eggs. In this context, the disclosure relates to the use of the previously described device

- for determining the degree of ageing of fuels and/or industrial operating materials, such as immersion baths, hydraulic oils and/or lubricants,
- for quality control, in particular of food and/or medicines,
- for determining a property of origin of the sample, in particular of food,
- for determining a degree of contamination of the sample, in particular of a surface,
- for detecting a falsification, and/or
- for detecting a change in the cell metabolism.

When detecting a change in the cell metabolism, per an embodiment, it is a case of detecting a change in the cell metabolism for purposes other than healing. More preferably, it is a case of detecting a change in the cell metabolism for non-diagnostic and/or non-therapeutic purposes.

BRIEF DESCRIPTION OF THE FIGURES

In the following, the disclosure is explained with reference to the accompanying drawings by way of exemplary embodiments, wherein the features presented below may each individually and in combination represent an aspect of the disclosure. In the drawings.

DETAILED DESCRIPTION

Figure 1:
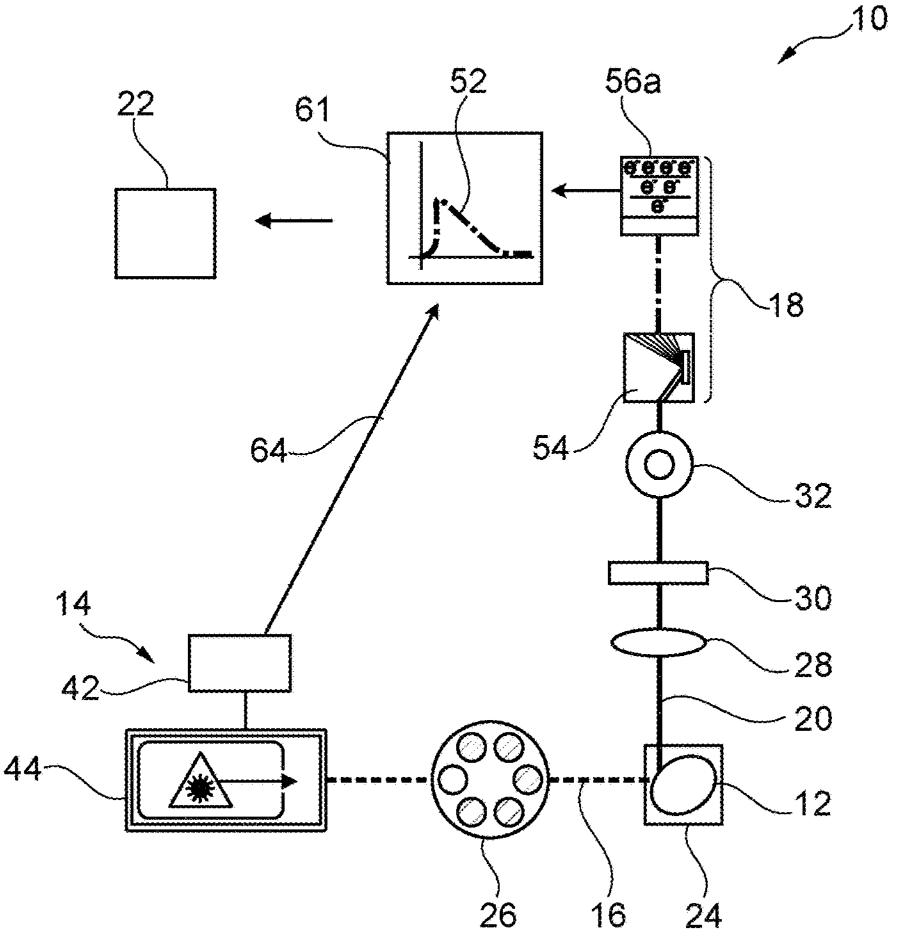
FIG. 1 is a schematic representation of a setup with a bird's egg and a device for in-ovo sex determination for this bird's egg according to an embodiment.

FIG. 1 shows a schematic representation of a device 10 for determining the sex of a fertilized bird's egg 12 according to an embodiment. The device 10 comprises a light source 14 for emitting pulsed excitation radiation 16, a detection device 18 for detecting autofluorescence radiation 20 emitted by the bird's egg 12, and a computer-based evaluation unit 22.

The detection device 18 is configured to detect the autofluorescence radiation 20 of the bird's egg 12 in a time-resolved manner at different wavelengths by means of time-correlated single photon counting (TCSPC) and to provide the evaluation device 22 with two-dimensional data with a wavelength dimension and a time dimen-sion. The evaluation device 22 is configured to classify the provided data into two classes by means of a classifier, wherein a first class represents a male sex of the fertilized bird's egg 12 and a second class represents a female sex of the fertilized bird's egg 12, and wherein features formed in the time dimension of the data are prioritized and taken into consideration at specific wavelengths during the classification.

In the present case, the bird's egg 12 is attached to a sample holder 24 and placed in the beam path in such a way that the freely propagating excitation radiation 16 from the light source 14 hits on the bird's egg 12. In addition, a variable laser beam attenuator 26 is provided between the light source 14 and the bird's egg 12 in order to reduce an excitation energy to an excitation energy suitable for TCSPC.

The autofluorescence radiation 20 emitted from an area inside the bird's egg 12 is detected by means of the detection device 18. For this purpose, the detection device 18 is arranged in relation to the bird's egg 12 in such a way that the autofluorescence radiation 20, which is emitted at an angle of approximately 90 degrees, hits onto the detection device 18 in a freely propagating manner. In order to focus the autofluorescence radiation 20 on the detection device 18, the device 10 comprises a lens 28 in the beam path between the bird's egg 12 and the detection device 18. In addition, the wavelength of the excitation radiation 16 that is scattered at the bird's egg 12 is filtered out by means of a long-pass filter 30 between the bird's egg 12 and the detection device 18. Before the autofluorescence radiation 20 hits onto the detection device 18, it is also attenuated by means of an aperture 32.

Figure 2:
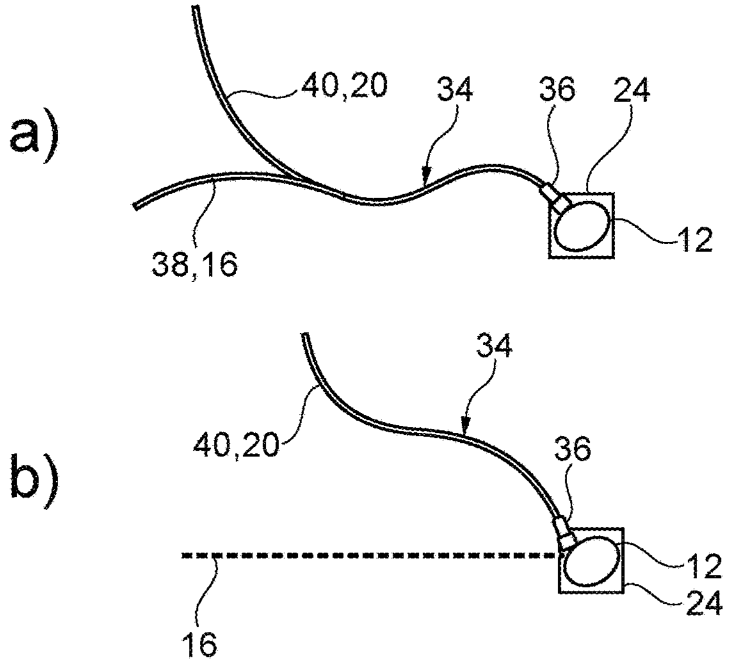
FIG. 2 is a schematic representation of two alternatives with regard to the guidance of the excitation radiation and the emitted autofluorescence radiation to the setup with bird's egg shown in FIG. 1 according to an embodiment.

In the embodiment shown in FIG. 1, the device 10 does not have a fiber-based light guide system 34 by means of which the light is directed onto the bird's egg 12 and/or onto the detection device 18. FIG. 2 shows two sections of the device 10 in alternative embodiments, in which the device 10 comprises a light guide system 34 with a measuring head 36.

In the variant shown in FIG. 2*a*), the light guide system 34 is configured Y-shaped and comprises two light guide strands 38, 40, one light guide strand 38 for the excitation radiation and one light guide strand 40 for the autofluorescence radiation 20. The two light guide strands 38, 40 are merged in the measuring head 36, so that the measuring head 36 is configured to emit the excitation radiation 16 onto the bird's egg 12 and to receive the autofluorescence radiation 20 emitted by the bird's egg 12.

In the variant shown in FIG. 2*b*, the light guide system 34 is configured as a simple light guide system and comprises only one light guide strand 40 for the autofluorescence radiation 20. The excitation radiation 16 continues to propagate freely from the light source 14 (not shown in FIG. 2) to the bird's egg 12. The measuring head 36 of the light guide system 34 is designed to receive the autofluorescence radiation 20 from the bird's egg 12.

Figure 3:
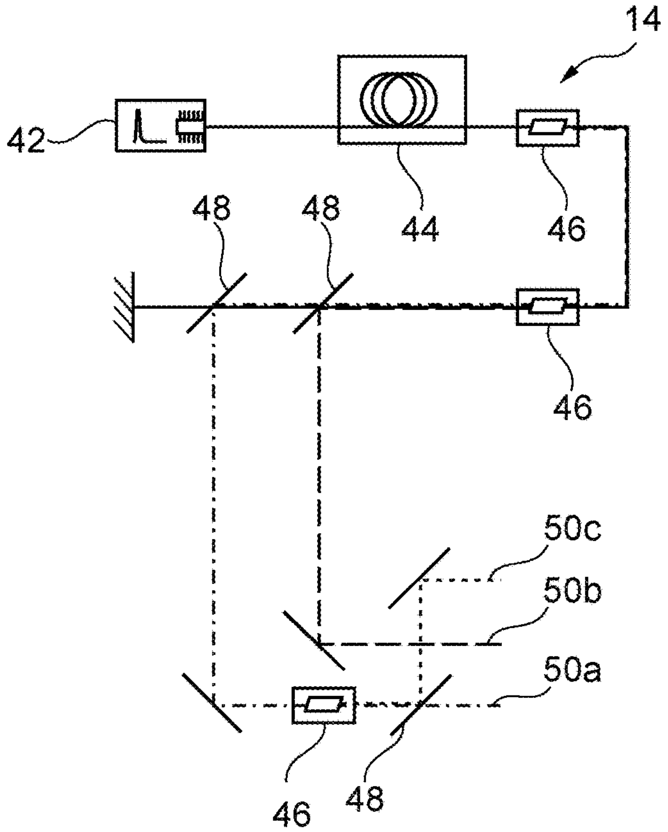
FIG. 3 is a schematic representation of a light source of the setup shown in FIG. 1.

FIG. 3 shows a schematic representation of the light source 14 of the setup shown in FIG. 1. The light source 14 is realized in the present case as a laser system 14 that generates excitation pulses with a pulse length of approximately 80 ps. The laser system 14 includes an infrared laser diode 42 that emits laser radiation at 1064 nm and is used as a master oscillator or seed laser to specify the characteristics of the laser emission of a multi-stage fiber amplifier 44. The birefringent crystals 46 and dichroic mirrors 48 present in the beam path allow the wavelengths of the second harmonic 50*a* (532 nm), the third harmonic 50*b* (355 nm) and the fourth harmonic 50*c* (266 nm) to be generated by means of nonlinear frequency conversion. In the setup shown in FIG. 1, the fourth harmonic 50*c* at 266 nm is used as the excitation radiation of the sample.

Figure 4:
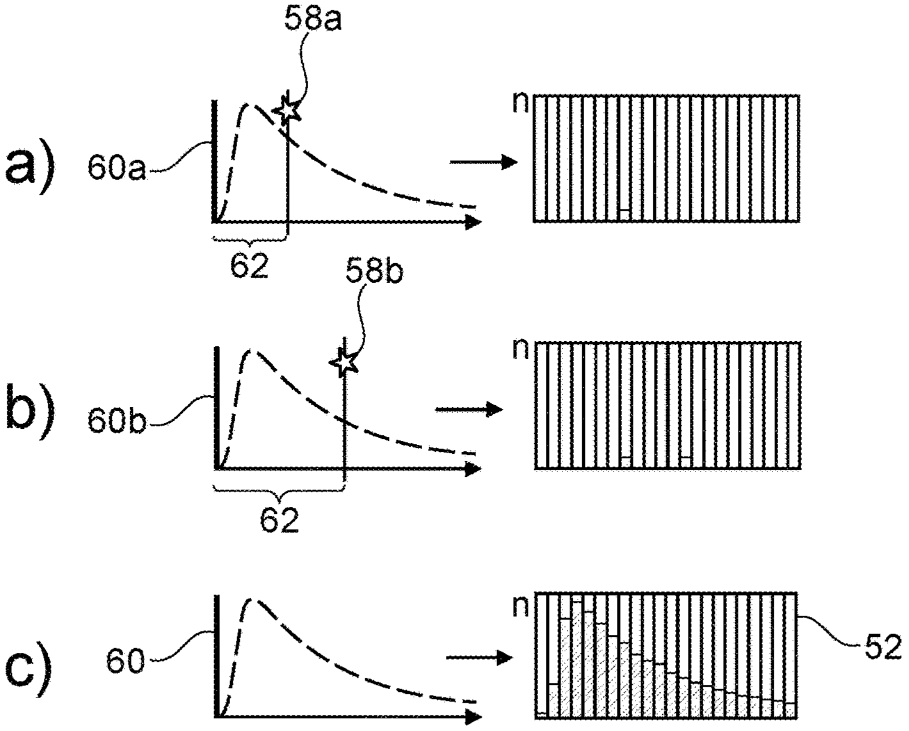
FIG. 4 is a schematic representation of the TCSPC histogram obtained by means of the device in FIG. 1, 5 or 6 according to an embodiment.

In conjunction with the detection device 18 shown in FIG. 1, FIG. 4 shows a schematic representation of the TCSPC histogram 52 determined during the detection of the autofluorescence radiation 20, which represents the time course of the autofluorescence radiation after excitation. As already mentioned, the detection de-vice 18 is configured to detect the autofluorescence radiation 20 of the bird's egg 12 in a time-resolved manner at several different wavelengths by means of TCSPC. To this end, the detection device 18 in the embodiment shown in FIG. 1 comprises a spectrometric device with a monochromator 54. As a detector element 56, the detection device 18 comprises a hybrid photomultiplier 56*a*. The monochromator 54 essentially consists of a diffraction grating that can be rotated in steps. The spectral range to be examined can be scanned by rotating the diffraction grating in steps.

Figure 5:
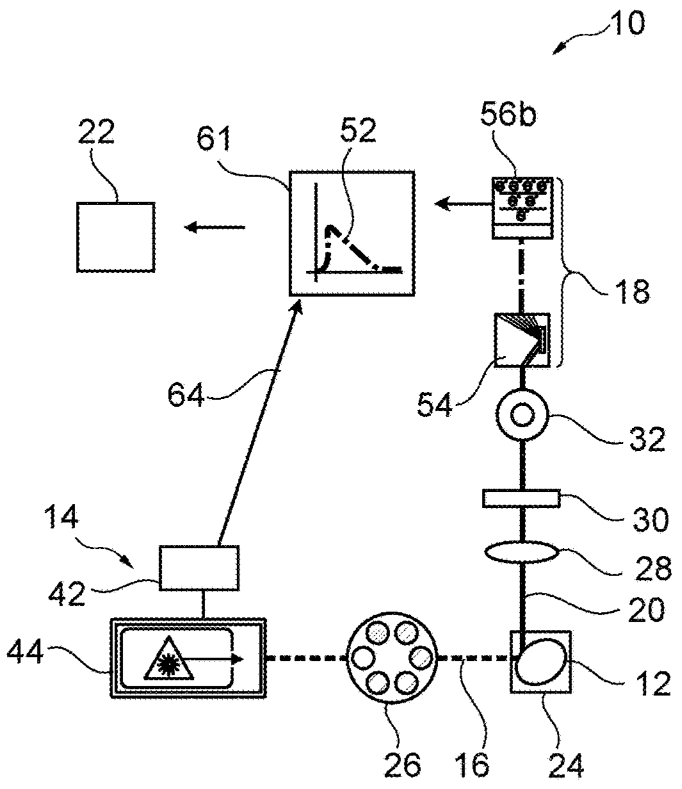
FIG. 5 is a schematic representation of an alternative setup to FIG. 1 of the device for in-ovo sex determination according to an embodiment.

FIG. 5 shows an alternative embodiment of the device 10, in which the detector element 56 is designed as an MCP-PMT 56*b*, which in the present case comprises 16 channels. In contrast to FIG. 1, moreover, the diffraction grating of the monochromator 54 is fixed in position. With this embodiment of the device 10, the spectral range to be examined can be "split" into up to 16 WL sub-intervals (detection channels).

Figure 6:
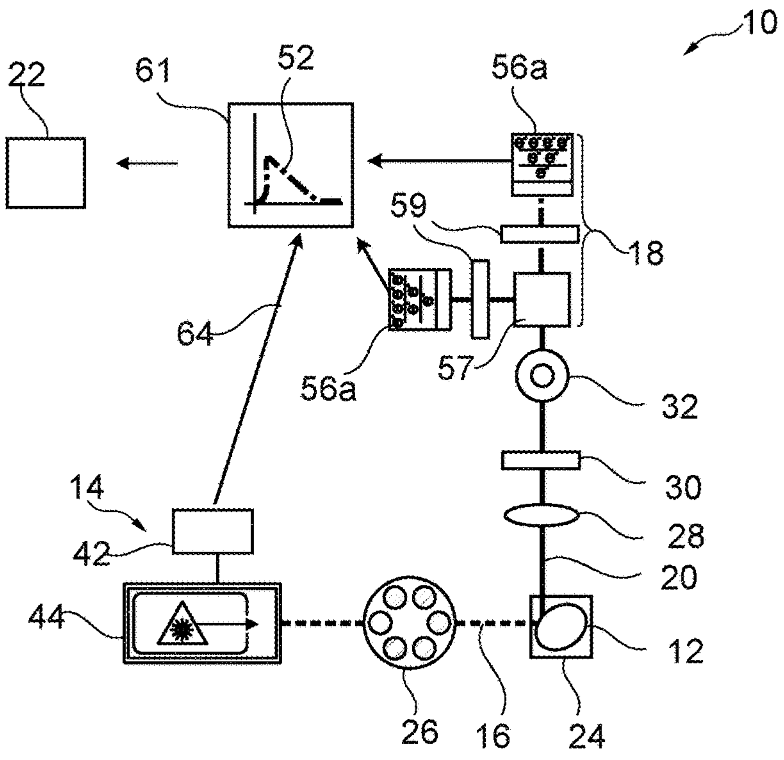
FIG. 6 is a schematic representation of a further alternative setup of the device for in-ovo sex determination according to an embodiment.

FIG. 6 shows a further alternative embodiment of the device 10, in which several detector elements 56 are used. Both detector elements 56 are configured as hybrid photomultipliers 56*a*, as in FIG. 1. Instead of a diffraction grating, a beam splitter 57 is used. Between the beam splitter 57 and the two hybrid PMTs 56*a*, an interference filter 59 is respectively interconnected which respectively transmits a specific wavelength.

In TCSPC, individual photons 58*a*, 58*b* of the autofluorescence radiation 20 are de-tected and the respective times 62 between an excitation pulse 60 of the pulsed excitation radiation 16 and the arrival of the respective photon 58 in the detection de-vice 18 are determined. For this purpose, the detection device comprises TCSPC electronics 61, which is schematically shown in FIGS. 1, 5, and 6. With reference to FIG. 4, the time measurement is started by the excitation pulse 60*a* and the photon 58*a* emitted during the transition from the excited state to the ground state stops the measurement (FIG. 4*a*). The process is repeated with the next excitation pulse 60*b* and the next photon 58*b* (FIG. 4*b*). By repeating the measurement many times, the TCSPC histogram 52 shown in FIG. 4*c* is obtained according to the measured times 62 of the individual photons 58. As indicated in FIGS. 1, 5 and 6, for measuring the time interval 62 the device 10 has an electrical connection 64 in order to transmit an electrical trigger signal, generated synchronously with the excitation pulse 60, to the detection device 18. The TCSPC electronics 61, which is schematically represented as a box in FIGS. 1, 5 and 6 and may, for example, be physically configured as a PC plug-in card, evaluates the signals and creates the TCSPC his-togram, which is output to the evaluation device 22 as two-dimensional data with a wavelength dimension and a time dimension.

The detection device 18 is therefore configured to detect the autofluorescence radia-tion 20 at several different wavelengths by means of TCSPC and to provide the evaluation device 22 with two-dimensional data. In the present case, the data are present as mathematical matrices $A\in\mathbb{R}$ m×n, wherein the matrix comprises m data points in the wavelength dimension, in the present example there are 74 data points. In the time dimension, the matrix comprises n data points, which enable the high time resolution necessary for the required accuracy, in the present example there are 250 data points:

wherein the rows of A, i.e. (aj1, . . . , ajn), j=1, . . . , m, each correspond to a TCSPC histogram and thus physically correspond essentially to the time-resolved measurements for certain fixed wavelengths.

In order to determine the sex of the fertilized bird's egg 12, a classifier classifies the provided data into two classes, wherein a first class represents a male sex of the fertilized bird's egg 12 and a second class represents a female sex of the fertilized bird's egg 12, wherein specific wavelengths to be prioritized are identified in the classification on the basis of features formed in the time dimension of the data, and a sex determination of the bird's egg 12 is carried out by prioritized consideration of the data at the specific wavelengths. In the present case, as classifier a linear classi-fier is used which separates the data along a hyperplane. The features formed in the time dimension of the data are in the present case the first three moments of the central moments of aj:=(aj1, . . . , ajn), j=1, namely mean value $\mu$, standard deviation $\sigma$ and skewness S.

As used herein, the terms "general," "generally," and "approximately" are intended to account for the inherent degree of variance and imprecision that is often attributed to, and often accompanies, any design and manufacturing process, including engineering tolerances, and without deviation from the relevant functionality and intended outcome, such that mathematical precision and exactitude is not implied and, in some instances, is not possible.

All the features and advantages, including structural details, spatial arrangements and method steps, which follow from the claims, the description and the drawing can be fundamental to the invention both on their own and in different combinations. It is to be understood that the foregoing is a description of one or more preferred exemplary embodiments of the invention. The invention is not limited to the particular embodiment(s) disclosed herein, but rather is defined solely by the claims below. Furthermore, the statements contained in the foregoing description relate to particular embodiments and are not to be construed as limitations on the scope of the invention or on the definition of terms used in the claims, except where a term or phrase is expressly defined above. Various other embodiments and various changes and modifications to the disclosed embodiment(s) will become apparent to those skilled in the art. All such other embodiments, changes, and modifications are intended to come within the scope of the appended claims.

As used in this specification and claims, the terms "for example," "for instance," "such as," and "like," and the verbs "comprising," "having," "including," and their other verb forms, when used in conjunction with a listing of one or more components or other items, are each to be construed as open-ended, meaning that the listing is not to be considered as excluding other, additional components or items. Other terms are to be construed using their broadest reasonable meaning unless they are used in a context that requires a different interpretation.

LIST OF REFERENCE NUMERALS

10 device
12 bird's egg
14 light source
16 excitation radiation
18 detection device
20 autofluorescence radiation
22 evaluation device
24 sample holder
26 variable laser beam attenuator
28 lens
30 long-pass filter
32 aperture
34 light guide system
36 measuring head
38 light guide strand
40 light guide strand
42 infrared laser diode
44 multilevel fiber amplifier
46 birefringent crystal
48 dichroic mirror
50 second to fourth harmonic of the laser wavelength 1064 nm

52 TCSPC histogram
54 monochromator
56*a* detector element, hybrid PMT
56*b* detector element, MCP-PMT
57 beam splitter
58 photon
59 interference filter
60 excitation pulse
61 TCSPC electronics
62 time between excitation pulse and detection of the photon
64 electrical connection

The invention claimed is:

1. A device for determining the sex of a fertilized bird's egg, comprising:

a light source for emitting pulsed excitation radiation;

a detection device for detecting autofluorescence radiation emitted by the fertilized bird's egg; and a computer-based evaluation unit, wherein the detection device is configured to detect the autofluorescence radiation of the fertilized bird's egg in a time-resolved manner at different wavelengths via time-correlated single photon counting and to provide the evaluation unit with two-dimensional data having a wavelength dimension and a time dimension, wherein the evaluation unit is configured to classify the provided data into classes via a classifier, wherein a first class represents a male sex of the fertilized bird's egg and a second class represents a female sex of the fertilized bird's egg, wherein the evaluation unit is configured to identify specific wavelengths to be prioritized during the classification on the basis of features formed in the time dimension of the data via machine learning, and wherein the evaluation unit is configured to take into consideration the data at the specific wavelengths in a prioritized manner in order to determine the sex of the fertilized bird's egg.

2. The device according to claim 1, wherein the light source is configured as a pulsed excitation laser system or as a pulsed LED.

3. The device according to claim 1, wherein the light source is configured to emit pulsed excitation radiation with a pulse repetition rate of ≥10 MHz, and/or wherein the light source is configured to emit pulsed excitation radiation having a pulse length of ≤500 ps, and/or wherein the light source is configured to emit pulsed excitation radiation having a pulse length of ≤5 ns.

4. The device according to claim 1, wherein the device comprises an optical attenuator in the beam path between the light source and the fertilized bird's egg for adjusting an energy of the excitation radiation.

5. The device according to claim 1, wherein the detection device for detecting the autofluorescence radiation at different wavelengths comprises a monochromator, a spectrograph, a beam splitter with a plurality of interference filters and/or a spectrometer, and/or wherein the detection device comprises as detector element a hybrid photomultiplier and/or a multichannel plate photomultiplier.

6. The device according to claim 1, wherein the device comprises a long-pass edge filter in the beam path between the fertilized bird's egg and the detection device for filtering a wavelength of the excitation radiation.

7. The device according to claim 1, wherein the device is configured to irradiate the fertilized bird's egg in free space with the excitation radiation and is configured such that the autofluorescence radiation emitted at an angle not equal to zero to the excitation radiation is directed in the free space onto the detection device.

8. The device according to claim 1, wherein the device comprises a measuring head, wherein a) the measuring head is configured to emit the excitation radiation into and/or onto the fertilized bird's egg, or b) the measuring head is configured to receive the autofluorescence radiation out of and/or from the fertilized bird's egg, or c) the measuring head is configured to transmit the excitation radiation into and/or onto the fertilized bird's egg and to receive the autofluorescence radiation out of and/or from the fertilized bird's egg.

9. The device according to claim 1, wherein the evaluation unit is configured to determine the sex of the fertilized bird's egg by taking into consideration the two-dimensional data.

10. A method for in-ovo sex determination in a fertilized bird's egg, the method comprising the steps of:

emitting pulsed excitation radiation for excitation of autofluorescence in an area in the interior of the bird's egg, on an egg membrane of the bird's egg and/or on the egg shell of the bird's egg via a light source;

time-resolved detection of the autofluorescence radiation emitted from the area inside, from the egg membrane and/or from the egg shell of the bird's egg via a detection device at different wavelengths by time-correlated single photon counting;

providing an evaluation device with two-dimensional data with a wavelength dimension and a time dimension by the detection device;

determining the sex of the fertilized bird's egg from the provided two-dimensional data via the evaluation device by classifying the provided data via a classifier into two classes, wherein a first class represents a male sex of the fertilized bird's egg and a second class represents a female sex of the fertilized bird's egg, wherein specific wavelengths to be prioritized are identified in the classification on the basis of features formed in the time dimension of the data via machine learning; and sex determination of the bird's egg by prioritized consideration of the data at the specific wavelengths.

* * * * *